United States Patent [19]

Adams et al.

[11] Patent Number: 4,778,805
[45] Date of Patent: Oct. 18, 1988

[54] 4,7-BENZOFURANDIONE DERIVATIVES USEFUL AS INHIBITORS OF LEUKOTRIENE SYNTHESIS

[75] Inventors: Julian Adams, Westmount; Yvan Guindon, Montreal; Patrice C. Belanger, Dollard des Ormeaux; Michel L. Belley, St. Laurent; Joshua Rokach, Chomedey, all of Canada

[73] Assignee: Merck Frosst Canada, Canada

[21] Appl. No.: 64,152

[22] Filed: Jun. 18, 1987

[51] Int. Cl.$^4$ .................... A61K 31/34; C07D 307/86
[52] U.S. Cl. .................... 514/320; 514/422; 514/452; 514/456; 514/464; 514/469; 514/470; 546/196; 548/525; 549/362; 549/398; 549/435; 549/466; 549/467; 549/468; 549/469; 549/470
[58] Field of Search .................... 546/196; 548/525; 549/362, 398, 435, 466, 467, 468, 469, 471; 514/320, 422, 452, 456, 464, 469, 470

[56] References Cited

U.S. PATENT DOCUMENTS 4,663,347  5/1987  Atkinson et al. .................... 514/469

OTHER PUBLICATIONS

Chem. Abstracts, 142937q, vol. 85 (1976).

Primary Examiner—Richard A. Schwartz
Assistant Examiner—Bernard I. Dentz
Attorney, Agent, or Firm—Gabriel Lopez; Hesna J. Pfeiffer

[57] ABSTRACT

4,7-Benzofurandione derivatives of Formula I, pharmaceutical compositions, and methods of treatment are disclosed. These compounds are useful as inhibitors of mammalian leukotriene biosynthesis. As such, these compounds are useful therapeutic agents for treating allergic conditions, asthma, cardiovascular disorders, inflammation, psoriasis and allergic conjunctivitis. The compounds are also useful as analgesics and as cytoprotective agents. Also disclosed are novel intermediates useful for the preparation of the 4,7-benzofurandiones of this invention.

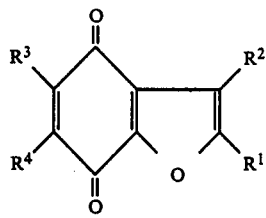

12 Claims, No Drawings

4,7-BENZOFURANDIONE DERIVATIVES USEFUL AS INHIBITORS OF LEUKOTRIENE SYNTHESIS

BACKGROUND OF THE INVENTION

This invention involves certain tetra-substituted 4,7-benzofurandione derivatives. A limited number of tetrasubstituted 4,7-benzofurandiones are described in the chemical literature (cfr. Chem. Abst. 41, 5507b (1947); ibid., 52, 12830g (1958); ibid., 84, 4756 (1976); ibid., 85, 142937 (1976 ). One of these compounds has been described a Precursor to a dye (Chem. Abst. 41, 5507b (1947)), but no biological utility has been described for these compounds, nor any direct utility for any of them.

The compounds of the present invention are useful as inhibitors of mammalian leukotriene biosynthesis. As such, these compounds are useful therapeutic agents for treating allergic conditions, asthma, cardiovascular disorders, inflammation, psoriasis and allergic conjunctivitis. The compounds are also useful as analgesics and as cytoprotective agents.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g., gall bladder). In addition, they promote mucous production, modulate vascular permeability changes, and are potent inflammatory agents in human skin. The most important compound in the second group of leukotrienes is Leukotriene $B_4$, a dihydroxy fatty acid. This compound is a potent chemotactic agent for neutrophils and eosinophils and, in addition, may modulate a number of other functions of these cells. It also affects other cell types such as lymphocytes and, for example, may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., Ann. Rpts. Med. Chem. 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. 5-lipoxygenase products are also thought to be regulators of mast cell degranulation and recent studies with human lung mast cells have suggested that 5-lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. 5-lipoxygenase inhibitors would therefore be a new class of drugs for the treatment of asthma. See, for example, B. Samuelsson, Science 220, 568–575 (1983).

Psoriasis is a human skin disease which affects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis, and gall bladder spasms. In addition, they may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function.

SUMMARY OF THE INVENTION

It has now been discovered that certain tetrasubstituted benzofurandiones of Formula I are effective inhibitors of leukotriene biosynthesis. Thus, these compounds are useful therapeutic agents for treating allergic conditions, asthma, cardiovascular disorders such as angina, inflammation, for amelioration of skin diseases like psoriasis and atopic eczema, for treatment of allergic conjunctivitis, as analgesics, and as cytoprotective agents.

DETAILED DESCRIPTION OF THE INVENTION

The compounds of the present invention are compounds of the formula:

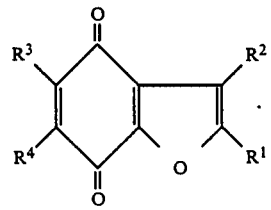

$R^1$ is $-(CR^5R^5)_l-(X^1)_m-(CR^5R^5)_n-\underset{Y^2}{\overset{Y^1}{\bigcirc}}$ ;

$-(CR^5R^5)_s-(X^1)_t-(CR^5R^5)_u-CO_2R^6$; or lower alkyl;

$R^2$ is lower alkyl;

$R^3$ and $R^4$ are each independently $R^2$, Cl, $X^2R^2$, or $X^3R^5$;

$R^5$ is H or lower alkyl, or two $R^5$'s when attached to N may be joined to form a 5- or 6-membered ring;

$R^6$ is H or lower alkyl;

$R^7$ is H or lower alkyl;

$R^8$ is H or lower alkyl;

$X^1$ is $X^2$ or $X^3$;

$X^2$ is S, S(O), S(O)$_2$;

$X^3$ is O or NR$^5$;

$X^4$ is $X^2$ or $X^3$ $Y^1$ and $Y^2$ are each independently: H, $R^2$, $X^2R^2$, $X^3R^5$, halogen, $(X^4)_w-(CR^5R^5)_z-CO_2R^7$, CF$_3$, COR$^8$, CONR$^5R^5$, or S(O$_2$)NR$^5R^5$; or $Y^1$ and $Y^2$ may be joined to form a 5- or 6-membered ring, containing one or two O atoms, such as —OCH$_2$O—, —OCH$_2$CH$_2$O—, —OCH$_2$CH$_2$— or —OCH$_2$CH$_2$CH$_2$—;

l and n are each independently 0 to 5;

m is 0 or 1;

s is 0 to 3;

u is 0 to 3 provided that when t is 1 and R$^6$ is H, then u is 1 to 3;

t is 0 or 1;

w is 0 or 1; and z is 0 to 3, provided that when w is 1 and R$^7$ is H, then z is 1 to 3;

and the pharmaceutically acceptable salts thereof.

A preferred embodiment of the present invention is represented by Formula Ia:

wherein:

$R^3$ is $R^2$ $R^4$ is $R^2$ or $X^3R^5$ n is 0 or 1 and the remaining substuents are as defined for Formula I.

Another preferred embodiment of the present information is that wherein:

$R^1$ is lower alkyl;

$R^3$ and $R^4$ are each independently $R^2$, $X^2R^2$, or $X^3R^5$; and the remaining substituents are as defined for Formula I.

Compounds of this invention are represented in Table 1.

TABLE 1

NOVEL TETRA-SUBSTITUTED 4,7-BENZOFURANDIONES

| Ex. No. | $R^1$ | $Y^1$ | $Y^2$ | $R^2$ | $R^3$ | $R^4$ |
|---|---|---|---|---|---|---|
| 1. | CO$_2$Et | — | — | Me | Cl | Cl |
| 2. | CO$_2$Et | — | — | Me | Me | Me |
| 3.* | CH$_2$C$_6$H$_3$Y$^1$Y$^2$ | 4-OMe | H | Me | Me | Me |
| 4. | CO$_2$Et | — | — | Me | n-Pr | OMe |
| 5. | CO$_2$Et | — | — | Me | n-Pr | Cl |
| 6. | CO$_2$Et | — | — | Me | n-Pr | SEt |
| 7. | CO$_2$Et | — | — | Me | n-Pr | S(O)Et |
| 8. | CO$_2$Et | — | — | Me | n-Pr | S(O)$_2$Et |
| 9. | CH$_2$C$_6$H$_3$Y$^1$Y$^2$ | 3-Cl | 4-OMe | Me | n-Pr | Cl |
| 10. | CH$_2$C$_6$H$_3$Y$^1$Y$^2$ | 4-OMe | H | Me | n-Pr | Me |
| 11. | CH$_2$C$_6$H$_3$Y$^1$Y$^2$ | 4-OMe | H | Me | n-Pr | SEt |
| 12. | CH$_2$C$_6$H$_3$Y$^1$Y$^2$ | 4-OMe | H | Me | n-Pr | S(O)Et |
| 13. | CH$_2$C$_6$H$_3$Y$^1$Y$^2$ | 4-OMe | H | Me | n-Pr | S(O)$_2$Et |
| 14.* | CH$_2$C$_6$H$_3$Y$^1$Y$^2$ | 4-OMe | H | Me | n-Pr | NH$_2$ |
| 15. | CH$_2$C$_6$H$_3$Y$^1$Y$^2$ | 4-OMe | H | Me | Me | n-Pr |
| 16.* | CH$_2$C$_6$H$_3$Y$^1$Y$^2$ | 4-OH | H | Me | Me | Me |
| 17.* | Et | — | — | Me | Me | Me |
| 18. | CH$_2$C$_6$H$_3$Y$^1$Y$^2$ | 3,4-OCH$_2$O | — | Me | Me | Me |
| 19. | (CH$_2$)$_2$—C$_6$H$_3$Y$^1$Y$^2$ | 4-OMe | H | Me | Me | Me |
| 20.* | CH(CH$_3$)C$_6$H$_3$Y$^1$Y$^2$ | 4-OMe | H | Me | Me | Me |
| 21. | SC$_6$H$_3$Y$^1$Y$^2$ | H | H | Me | Me | Me |
| 22. | SCH$_2$CO$_2$Me | — | — | Me | Me | Me |
| 23. | SCH$_2$CO$_2$H | — | — | Me | Me | Me |
| 24.* | C$_6$H$_3$Y$^1$Y$^2$ | H | H | Me | Me | Me |

*Preferred Compounds

As used herein, "halogen" is F, Cl, Br, or I.

As used herein, the term "lower alkyl" includes those alkyl groups of from 1 to 7 carbon atoms of either a straight, branched, or cyclic configuration. Examples of "lower alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like.

It is intended that the definitions of any substituent (e.g., $R^5$, $X^2$, $X^3$, etc.) in a particular molecule is independent of its definitions elsewhere in the molecule. Thus, CR$^5R^5$ represents CH(CH$_3$)$_2$, CH$_2$, C(CH$_3$)$_2$, etc.

Abbreviations used throughout are as follows: Me is methyl, Et is ethyl, n-Pr is normal propyl, Ac is acetyl, C$_6$H$_3$Y$^1$Y$^2$ is

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

The term "Pharmaceutically acceptable salts" refers to salts prepared from pharmaceutically acceptable non-toxic bases including organic and inorganic bases, and from pharmaceutically acceptable non-toxic acids, including organic and inorganic acids.

When the compound of the present invention is acidic, pharmaceutically acceptable salts may be prepared from the appropriate base. Salts derived from inorganic bases include aluminum, ammonium, calcium, copper, ferric, ferrous, lithium, magnesium, manganic, manganous, potassium, sodium, zinc salts, and the like. Particularly preferred are the ammonium, calcium, magnesium, potassium and sodium salts. Salts derived from organic bases include salts of primary, secondary, and tertiary amines, substituted amines including naturally occurring substituted amines, cyclic amines and basic ion exchange resins, such as arginine, betaine, caffeine, choline, N,N'-dibenzylethlenediamine, diethylamine, 2-diethylaminoethanol, 2-dimethylaminoethanol, ethanolamine, ethylenediamine, N-ethyl morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, pharmaceutically acceptable salts may be prepared from the appropriate acid. Such acids include acetic, benzensulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, panoic, pantothenic, phosphoric, succinic, sulfuric, tataric acid, P-toluenesulfonic, and the like. Particularly preferred are citric, hydrobromic, hydrochloric, maleic, phosphoric, sulfuric, and tartaric acids.

A further embodiment of this invention are novel di- and tri-substituted compounds of Formula Ib useful as intermediate for the preparation of Formula I compounds. These compounds are represented in table 2.

TABLE 2

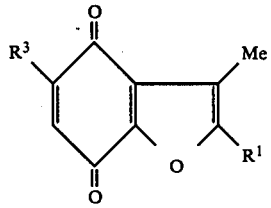

Ib

| Ex. No. | R¹ | Y¹ | Y² | R³ |
|---|---|---|---|---|
| 25 | CO$_2$Et | — | — | H |
| 26 | CO$_2$Et | — | — | n-Pr |

TABLE 2-continued

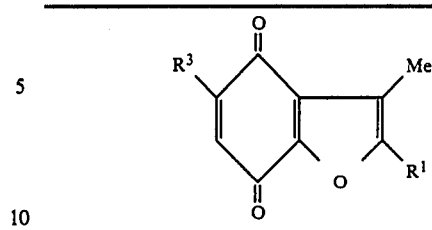

Ib

| Ex. No. | R¹ | Y¹ | Y² | R³ |
|---|---|---|---|---|
| 27 | H | — | — | n-Pr |
| 28 | CH$_2$C$_6$H$_3$Y¹Y² | 4-OMe | H | n-Pr |
| 29 | CH$_2$C$_6$H$_3$Y¹Y² | 4-OH | H | n-Pr |
| 30 | CH$_2$C$_6$H$_3$Y¹Y² | 4-OMe | H | H |
| 31 | CH$_2$CO$_2$Et | — | — | n-Pr |

The following reaction schemes illustrate the preparation of compounds of the present invention:

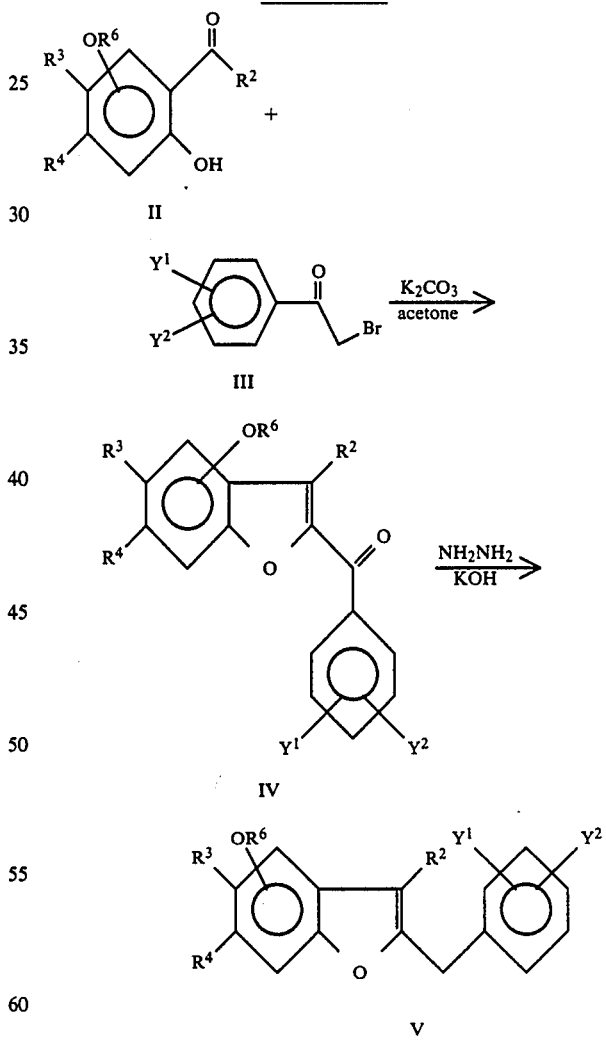

SCHEME I

A suitable acetophenone (II) is reacted with a substituted phenacyl bromide (III) at a temperature ranging from room temperature to about 150° C. in an inert solvent (preferably at reflux in acetone) on the presence of a base (for example, an alkali metal hydroxide or carbonate) to give the corresponding benzoyl benzofuran derivative (IV). The compound of the formula IV is then reduced to give V. For example, subsequent treatment of IV with hydrazine and a strong base at a temperature of about 150° to 210° C. preferably using the Huang Minlon modification of Wolff-Kishner conditions (J. Am. Chem. Soc. 68, 2487 (1946)) yields the desired benzyl benzofuran derivative V. Alternatively, compound IV can be reduced to compound V using zinc amalgam and a strong acid (preferably hydrochloric acid). See, for example, Ber. 46, 1837 (1913). Alternatively, compound IV can be reduced to compound V using a mixture of lithium aluminum hydride and aluminum chloride in ether or tetrahydrofuran as solvent at a temperature range varying from 0° C. to 65° C.

SCHEME II

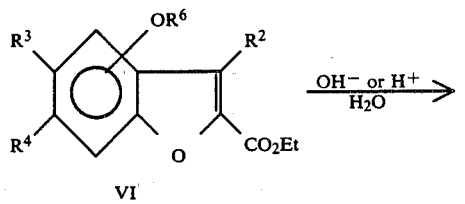

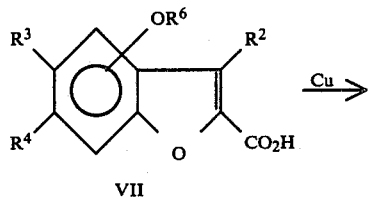

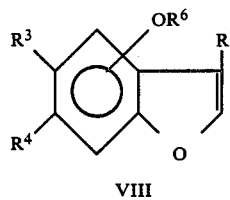

According to the method of Scheme II, hydrolysis of an appropriate compound of the formula VI with a strong acid or a strong base in water, or a mixture of water and an organic water-soluble solvent, such as methanol, ethanol, tetrahydrofuran, etc. at a temperature ranging from room temperature to reflux (preferably, reflux) yields the corresponding acid of formula VII. Compounds of the formula VI are disclosed in EP 146,243, published June 26, 1985. The acid of formula VII is then decarboxylated to yield the corresponding benzofuran derivative of the formula VIII. This may be done by heating the acid in quinoline in the presence of copper. It can also be done by heating at reflux compound VII with a strong acid such as hydrochloric acid in a two-phase system made up of toluene and aqueous acid. Benzene or xylene or other aromatic hydrocarbons can be substituted for toluene.

SCHEME III

[Scheme III structures showing compound VIII + R⁹COCl with Lewis Acid giving compound X, then reducing to compound XI]

$R^9$ is loweralky, or $C_6H_3Y^1Y^2$.

Following Scheme III, Compound VIII, which is unsubstituted in position 2, can be reacted with an acid halide IX in the presence of a Lewis acid, preferably aluminum chloride, to yield the 2-acyl derivative X. This reaction is best carried out in a solvent such as methylene chloride or ethylene dichloride at a temperature ranging from 0° to 25° C. The compound of the Formula X is then reduced to give the compound of Formula XI. For example, subsequent treatment of X with hydrazine and a strong base at a temperature of about 150° to 210° C. using the Huang-Minlon modification of Wolff-Kishner conditions (J. Am. Chem. Soc. 68, 2487 (1946)) yields the desired alkyl benzofuran derivative XI. Alternatively, compound X can be reduced to compound XI using zinc amalgam and a strong acid (preferably hydrochloric-acid). See, for example, Ber., 46, 1837 (1913).

Alternatively, compound X can be reduced to compound XI using a mixture of lithium aluminum hydride and aluminum chloride in ether or tetrahydrofuran as solvent at a temperature range varying from 0° to 65° C.

SCHEME IV

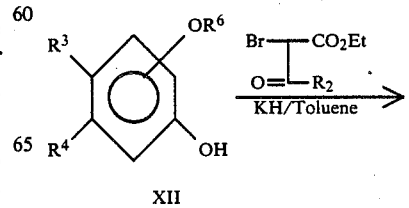

-continued
SCHEME IV

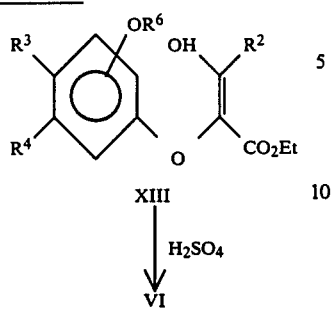

XIII

↓ H₂SO₄

VI

An alternative method to prepare ester VI of Scheme II is shown is Scheme IV. The substituted phenol may be O-alkylated with a suitable bromoester and cyclized using concentrated H₂SO₄ to form benzofuran ester VI.

SCHEME V

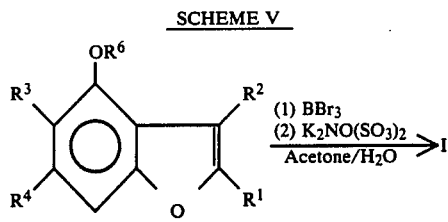

V or XI

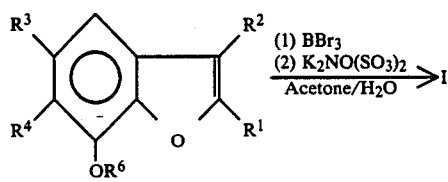

V or XI

Oxidation of a phenol V or XI to the corresponding 4,7-benzofurandione I is conveniently achieved using Fremy's salt (K₂NO(SO₃)₂) in acetone/water at 50° C. An alternative oxidative method employs a catalytic amount of bis(salicylidene)ethylenediiminecobalt (II) (salcomine) (see Parker, Tet. Lett., 22 397–400(1981)) or related catalysts described in Frostin-Rio, J. Chem. Soc. Perkin Trans. 1, 1971 (1984), dissolved in a suitable solvent such as dimethylformamide (DMF), with stirring in the presence of air.

When R⁶ in V or XI is lower alkyl, the compound is first converted to the corresponding phenol (R=H) by treatment with BBr₃.

SCHEME VI

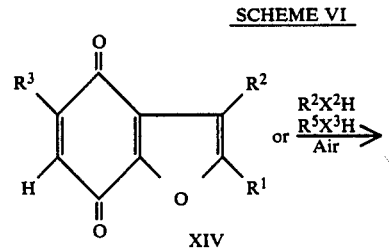

XIV

-continued
SCHEME VI

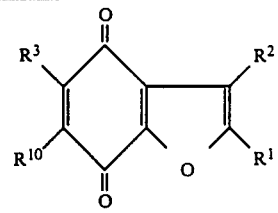

Substitution of the 4,7-benzofurandione XIV by R²X² or R⁵X³ can be achieved by oxidative addition by a 1,4 conjugate Michael type reaction in the presence of air as illustrated in Scheme VI, wherein R¹⁰ is R²X² or R⁵X³.

SCHEME VII

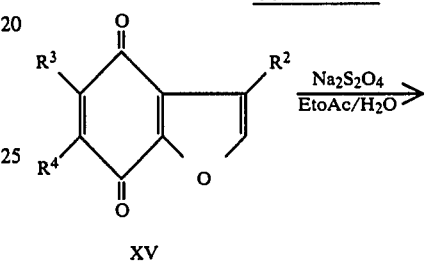

XV

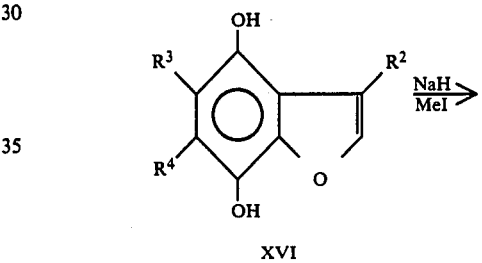

XVI

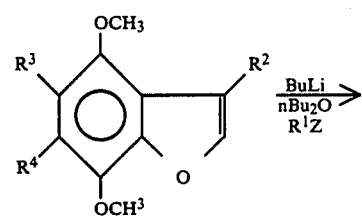

XVII

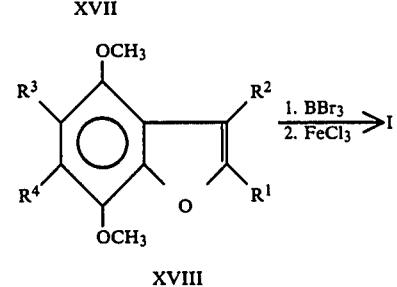

XVIII

Substitution at the 2-position of the 4,7-benzofurandione XV may be achieved following Scheme VII. Reductive methylation produces benzofuran XVII, which can be lithiated at the 2-position and reacted with suitable electrophiles. The dimethoxy benzofuran XVIII can be demethylated and re-oxidized to give the tetrasubstituted 4,7-benzofurandione I. In Scheme VII, Z is a leaving group such as a sulfide, halogen, tosylate, or mesylate.

The compounds of Formula I may be tested using one or more of the following assays to determine their mammalian leukotriene biosynthesis inhibiting activity and other relevant activities.

RBL-1 5-Lipoxygenase

Rat basophilic leukemia (RBL-1) cells are sonicated and centrifuged at 125000 xg. The resulting supernatant fraction is incubated with arachidonic acid (labelled with $^{14}C$) to convert a portion of it to $^{14}C$-5(S)-hydroxyicosatetraenoic acid (5-HETE). Compounds being evaluated as inhibitors of 5-Lipoxygenase are added prior to the addition of arachidonic acid. 5-HETE is isolated by extraction and paper chromatography, and quantitated by determining the amount of radioactivity (cpm) associated with 5-HETE.

Reference: Egan, R. W.; Tischler, A. M.; Baptista, E. H.; Ham, E. A.; Soderman, D. D.; and Gale, P. H.; *Advances in Prostaglandin, Thromboxane and Leukotriene Research*, 11, 151, (1983), (Samuelsson, B.; Ramwell, P. W.; and Paoletti, R.; (eds.), Raven Press, N.Y.

Mouse Macrophase Assay

Mouse peritoneal macrophages are treated sequentially with arachidonic acid (labelled with tritium); the compound being evaluated as an inhibitor, and a stimulator (zymosan). Metabolites derived from arachidonic acid ($PGE_2$, 6-keto $PG-F_{1a}$ and leukotriene $C_4$) are separated from the incubation medium by extraction and chromatography, and then quantitated by determining the amount of radioactivity (cpm) associated with each of them. Inhibitors cause a reduction in the amount of radioactivity (cpm) associated with a given metabolite. (This protocol is identical to that described in the reference except that the radioactivity herein associated with the $LTC_4$ is determined by counting an aliquot of the final aqueous solution directly rather than chromatographing it first.

Reference: Humes, J. L. et al., *J. Biol. Chem.*, 257, 1591–4, (1982).

Rat Polymorphonuclear Leukocyte (P.M.N.) Assay

Rats under ether anesthesia are injected (intraperitoneally) with 8 ml of a suspension of sodium caseinate (6 grams in about 50 ml water). After 15 to 24 hours the rats are sacrificed ($CO_2$) and the cells from the peritoneal cavity are recovered by lavage with 20 ml of buffer (Eagles Minimal Essential Medium containing 30 mM HERPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/ml. A 500 $\mu$aliquot of the suspension (PMN) and test compound are preincubated for 2 minutes at 37° C., followed by the addition of 10 $\mu$M 1 A-23187 calcium ionophore (Calbiochem). The suspension is stirred for an additional 4 minutes then bioassayed for $LTB_4$ content by adding an aliquot to a second 500 $\mu$l portion of the PMN at 37° C. The $LTB_4$ produced in the first incubation causes aggregation of the second PMN, is measured as a change in light transmission. The size of the assay aliquot is chosen to give a submaximal transmission change (usually −70%) for theuntreated control. The percentage inhibition of $LTB_4$ formation is calculated from the ratio of transmission change in the sample to the transmission change in the compound-free control.

Antigen Challenge 'in vitro' Assay

Male guinea pigs weighing 300–350 g are sensitized by injecting (intraperitoneally) 0.5 ml of a suspension containing 0.4 mg of egg albumin (Ovalbumin, Grade V, Sigma Chemical Co.) and 4.0 g aluminum hydroxide in 19.6 ml of saline. Two weeks are permitted for sensitization to occur.

Three sensitized guinea pigs are stunned and exanguinated. The tracheas are removed, freed of adhering tissue and divided longitudinally by cutting through the cartilaginous tissue directly opposite the muscle insertion. Each opened trachea is then transected between every second cartilage. Four of the cut sections are tied together, end to end, in a series with No. 7 silk thread ensuring that the tracheal muscles are all in the same vertical plane. Thus, each chain consists of tissue from three different animals.

The chain so formed is then suspended under 1 g of tension (by silk ties at each end) in a 20 ml organ bath containing 10 ml of modified[1] KrebsHenseleit buffer solution gassed with 95% $O_2$ and 5% $CO_2$ at 37° C. Mepyramine (0.55 $\mu$g/ml) and indomethacin (2.67 $\mu$g/ml) are added to the buffer to avoid the contribution of histamine receptors and cyclooxygenase products to the contraction. To record responses one end of the tracheal chain is attached to a Gould-Statham UC-2 force displacement transducer which is connected to a Beckman Type R-dynograph. The preparations are allowed to equilibrate for one hour during which time the tissues are automatically washed (10 ml volume displacement) every 6 minutes.

[1]modified Krebs solution in grams/liter and (mM): NaCl—6.87 (120); glucose 2.1 (11); $NaHCO_3$—2.1 (25); KCl—0.32 (4.72); $CaCl_2$—0.28 (2.5); $MgSO_4.7H_2O$—0.11 (0.5); $KH_2PO_4$—0.16 (1.2); pH at bathing solution=7.35±0.05.

After the equilibration period the tissues are primed with methacholine (3 $\mu$g/ml; 1.5×10$^{-5}$M), washed and allowed to recover to baseline. The tissues are treated again with a second dose of methacholine, washed, allowed to return to baseline and washed for an additional hour.

Two chains are used as a control. These are incubated in a concentration of egg albumin sufficient to induce an average contraction of 50–80% of the methacholine response.

Each compound to be tested is added to two other baths (at a final concentration in each bath of 10 $\mu$g/ml 15 minutes prior to challenging the fresh chains with egg albumin.

The response of the challenged tissue is expressed as a percentage of the methacholine maximum. The percentage inhibition for each compound is then calculated. Compounds which at 10 $\mu$g/ml (final concentration) inhibit the egg albumin response by 50% or more are retested at a lower concentration.

Asthmatic Rat Assay

Rats are obtained from an inbred line of asthmatic rats. Both female and male rats from 200 to 300 g are used.

Egg albumin (EA), grade V, crystallized and lyophilized, is obtained from Sigma Chemical Co., St. Louis. *Bordetella pertussis* vaccine, containing 30×10$^9$ killed bacteria per ml is obtained from the Institute Armand-Frappier, Laval des Rapides, Quebec. Aluminum hydroxide is obtained from the Regis Chemical Company, Chicago.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 ml of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 ml of a suspension containing 1 mg EA and 200 mg aluminum hydroxide in saline. Simultaneously, they receive an injection (intraperitoneally) of 0.5 ml of *B. Pertussis* vaccine. They are used between days 14 and 18 postsensitization. In order to eliminate the serotonin component of the response, rats are pretreated intravenously 5 minutes prior to aerosol challenge with 30 gm/kg methylserzide. Rats are then exposed to an aerosol of 3% EA in saline for exactly 1 minute, then their respiratory profiles are recorded for a further 25 to 30 minutes. The duration of continuous dyspnoea is measured from the respiratory recordings.

Compounds are generally administered either intraperitoneally 1 hour prior to challenge or orally 1 and ½ hours prior to challenge. They are either dissolved in dimethylsulfoxide or suspended in 0.1% methocel and 0.5% Tween 80. The volume injected is 2 ml/kg (intraperitoneally) or 10 ml/kg (orally). Prior to oral treatment rats are starved overnight. Their activity is determined in terms of their ability to decrease the duration of symptoms of dyspnoea in comparison with a group of vehicle-treated controls. Usually, a compound is evaluated at a series of doses and an $ED_{50}$ is determined. This is defined as the dose (mg/kg) which would inhibit the duration of symptoms by 50%.

PAF-Induced Hyperalgesia Assay

Female Sprague-Dawley rats, 35 to 40 g are fasted overnight. Platelet activating factor, PAF,(L-lecithin B-acetyl O-alkyl) 1 μg/0.1 ml is given by subplantar injection in the rat paw. The compounds to be evaluated are homogenized in Aqueous Vehicle (0.9% benzyl alcohol, 0.5% Tween 80 and 0.4% methylcellulose) and administered orally in a volume of 0.1 ml, 30 minutes prior to PAF.

Animals are tested 1, 2, 3 and 4 hours after PAF administration. The vocalization threshold, defined as the pressure (mmHg) needed to evoke a squeak response, was recorded for both the injected and contralateral paw. No animal is subjected to pressure greater than 60 mmHg. Hyperalgesia is defined as a decrease in vocalization threshold as compared to a normal paw. Percent inhibition of hyperalgesia is calculated as the proportion of animals with vocalization thresholds greater than 200% of controls.

Brewer's Yeast Hyperalgesia Assay

The standard method [Winter, C. A. et al., *J. Pharm. Exp. Ther.* 150, 165–171 (1965)] for yeast hyperalgesia is used. Female Sprague-Dawley rates, 35–40 g are fasted overnight. A 5% solution (volume 0.1 ml) of Brewer's yeast is injected into the rat paw. The compound is homogenized in aqueous vehicle and given orally 2 hours after yeast. Vocalization thresholds are recorded 1 hour after drug (3 hours after yeast). Percent inhibition of hyperalgesia is determined by the proportion of animals with vocalization thresholds greater than 25 mmHg.

The compounds of the Formula I have unexpected activity as inhibitors of the mammalian biosynthesis of leukotriene $B_4$, as well as leukotrienes $C_4$, $D_4$, $E_4$ and $F_4$, the active elements of the slow reacting substance of anaphylaxis (SRS-A). The compounds of Formula I are thought to act as inhibitors of the mammalian 5-lipoxygenase enzyme system of the arachidonic acid cascade. This inhibition of the mammalian biosynthesis of leukotrienes indicates that the compositions are useful to treat, prevent or ameliorate, in mammals and especially in humans 1) pulmonary conditions including diseases such as asthma, 2) allergies and allergic reactions such as allergic rhinitis, contact dermatitis allergic conjunctivitis and the like, (3) inflammation such as arthritis, (4) pain, (5) skin conditions such as psoriasis and the like, and (6) cardiovascular conditions such as angina and the like, and that the compounds are cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue, liver parenchymal damage caused by hepatoxic agents such as $CCl_4$ and D-galactosamine; ischemic renal failure; disease-induced hepatic damage, bile salt induced pancreatic or gastric damage; trauma- or stress-induced cell damage; and glycero-induced renal failure.

The cytoprotective activity of a compound may be observed in both animal and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay.

A. Ethanol-Induced Gastric Ulcer Assay

Twenty-four hour fasted Sprague-Dawley (S.D.) rats are perorally (p.o.) does with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosa are examined for resulting lesions.

B. Indomethacin-Induced Ulcer Assay

Indomethacin, 10 mg/kg p.o., is used to induce ulcers in 24 hour fasted S. K. rats. Fifteen minutes prior to indomethacin administration, groups of rats each receive either an aqueous vehicle (5% by weight methylcellulose) or the test compound at various doses perorally. Four hours later the animals are sacrifices and stomach mucosa are examined for resulting ulcers.

The magnitude of a prophylactic or therapeutic dose of a compound of formula I will, of course, vary with the nature of the severity of the condition to be treated and with the particular compound of formula I and its route of administration. When a compound of formula I is used in a pharmaceutical composition, the effective concentration in the composition will vary as required by the mode of administration, dosage form and pharmocological effect and level desired. In general, the daily dose range for anti-asthmatic, anti-allergic or anti-inflammatory use and, generally, uses other than cytoprotection lies within the range of from about 0.01 mg to about 100 mg per kg body weight of a mammal. This dosage may be administered in a single or divided individual doses. More or less of the general daily dosage may be necessary depending upon the individual needs of the patient.

The exact amount of a compound of the Formula I to be used as a cytoprotective agent will depend on, inter alia, whether it is being administered to heal damaged cells or to avoid future damage, on the nature of the damaged cells or to avoid future damage, on the nature of the damaged cells (e.g., gastro-intestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of FormulaI is administered from 30 minutes prior up to 30 minutes after administration of the NSAID (for example, in a combination dosage form). Preferably it is administered prior to or simultaneous with the NSAID.

The effective daily dosage level for compounds of Formulae I inducing cytoprotection in mammals, especially humans, will generally range from about 0.002 mg/kg to about 100 mg/kg, preferably from about 0.02 mg/kg to about 30 mg/kg. The dosage may be administered in single or divided doses.

Any suitable route of administration may be employed for providing a mammal, especially a human, with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release capsules and the like. Parenteral dosage forms include solutions, emulsions and the like. Dosage forms for administration by inhalation including sprays, aerosols and the like. These inhalation formulations may be administered in metered doses ranging from about 0.1 $\mu$g to about 200 $\mu$g, administered as needed.

For treating allergies or allergic reactions, such as allergic conjunctivitis, allergic rhinitis and the like, the Formula I compound may be administered by any conventional mode, e.g., orally, parenterally, topically, subcutaneously, by inhalation and the like. The oral and parenteral dosage forms are the same type as for the pulmonary treatment. The topical application dosage forms include ointments, salves, controlled release patches, emulsions, solutions, thixotropic formulations, powders, sprays and the like. For topical application, the percent by weight active ingredient (Formula I compound) may vary from about 0.001 to about 10%.

For treating inflammation the mode of administration may be oral, parenteral, by suppository and the like. The various dosage forms are the same as those described above.

For treating skin diseases such as psoriasis, atopic dermatitis and the like, oral, topical or parenteral administration is useful. For topical application to the diseased area salves, patches, controlled release patches, emulsions, etc., are convenient dosage forms.

For use as an analgesic, i.e., for treating pain, any suitable mode of administration may be used, e.g., oral, parenteral, by insufflation, by suppository and the like.

For treating cardiovascular conditions such as angina pectoris, etc., any suitable mode of administration, e.g. oral, parenteral, topical, insufflation, etc. and dosage form e.g. pills, liquid formulations, controlled release capsules, controlled release skin patches, etc. may be used.

The compositions include compositions suitable for oral, rectal, ophthalmic, pummonary, nasal, dermal, topical or parenteral (including subcutaneous, intramuscular and intravenous) administration, although the most suitable route in any given case will depend on the nature an severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use and, generally, uses other than cytoprotection is from about 0.01 mg to about 20 mg (preferably from about 0.1 mg to about 10 mg) of a compound of Formula I per kg of body weight per day and for cytoprotective use from about 0.002 mg to about 100 mg (preferably from about 0.02 mg to about 30 mg and more preferably from about 0.1 mg to about 10 mg) of a compound of Formula I of body weight per day. In the case where an oral composition is employed, a suitable dosage range for anti-asthmatic, anti-inflammatory or anti-allergic use and, generally, uses other than cytoprotection is from about 1 to about 100 of a compound of Formula I per kg of body weight per day, preferably from about 5 mg to about 40 mg per kg and for cytoprotective use from about 0.01 mg to about 100 mg (preferably from about 0.1 mg to about 30 mg and more preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition form inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, leukotriene antagonists of Formula I can be combined as the active ingredient in intimate admixture with a pharmaceutical carrier according to conventional pharmaceutical compounding techniques and using conventional ingredients, e.g. diluents, carriers, etc. The carrier may take a wide variety of forms depending on the form of preparation desired form administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets and capsules represent the most advantageous oral dosage unit form, in which case solid pharmaceutical carriers are obviously employed. If desired, tablets may be sugar coated or enteric coated by standard techniques.

In addition to the common dosage forms set above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are incorporated herein by reference.

Dosage forms for application to treat the eye are disclosed in U.S. Pat. No. 4,348,398, the disclosure of which is incorporated herein by reference.

Pharmaceutical compositions of the present invention suitable for oral adminstration and by inhalation in the case of asthma therapy may be presented as discrete units such as capsules, cachets or tablets each containing an predetermined amount of the active ingredient, as a powder or granules or as a solution or suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing formsuch as powder or granules, optionally mixed with a binder, lubricant, inert diluent, lubricating, surface active or dispersing agent. Molded tablets may be made by molding in a suitable machine, a mixture of the powdered compound moistened with an inert liquid diluent Desirably, each tablet contains from about 25 mg to about 500 mg of the active ingredient and each cachet or capsule contains from about 25 to about 500 mg of the active ingredient.

The following are examples of representative pharmaceutical dosage forms:

| Injectible Suspension | mg/mL |
|---|---|
| Compound of Formula I | 2 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Aerosol for Oral Inhibition | mg/can (200 doses/can) |
|---|---|
| Compound of Formula I | 2–40 |
| Oleic Acid | 0.2–4.0 |
| Trichloromonofluoro methane | 5,000–8,000* |
| Dichloromonofluoro methane | 15,000–12,400* |

| Cream | mg/g |
|---|---|
| Compound of Formula I | 1–100 |
| Cetyl alcohol | 130.0 |
| Sodium Lauryl Sulfate | 15.0 |
| Propylene Glycol | 100.0 |
| Benzalkonium chloride | 1.5 |
| Purified Water of sufficient quantity to make total 1 g | |

| Ointment | mg/g |
|---|---|
| Compound of Formula I | 1–100 |
| Benzalkonium chloride | 1.5 |
| Petrolatum of sufficient quantity to make total 1 g | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

*To a total of 20,400

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na³⁰ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

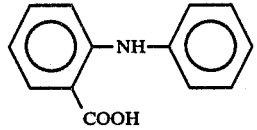

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

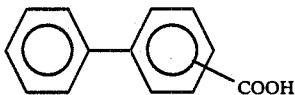

which can bear a variety of substituents and in which the free —COOH group can be in the form of a pharmaceutically acceptable salt group, e.g., —COO⁻Na⁺.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

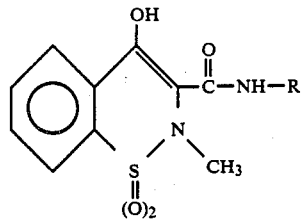

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., Pharmaprojects), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 130,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP application Nos. 56,172 (July 21, 1982) and 61,800 (June 10, 1982); and in U.K. patent specification No. 2,058,785 (Apr. 15, 1981). which are hereby incorporated herein by reference.

Pharmaceutical compositons comprising the Formula I compounds may also contain as the second active ingredient, prostaglandin antgonists such as those disclosed in EP 11,067 (May 28, 1980) or thromboxane antagonists such as those disclosed in U.S. Pat. No. 4,237,160. They may also contain histidine decarboxylase inhibitors, such as α-fluoromethyl histidine, described in U.S. Pat. No. 4,325,961. The compounds of the Formula I may also be advantageously combined with an $H_1$ or $H_2$-receptor antagonist, such as for instance benadryl, framamine, histadyl, phenergan, terfenadine, acetamazole, cimetidine, ranitidine, famotidine, aminothiadiazoles disclosed in EP 40,696 (Dec. 2, 1981) and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No.4,255,431, and the like. Compounds of Formula I may also be usefully combined with most cell stabilizing agents, such as 1,3-bis(2-carboxychromon-5-yloxy)-2-hydroxypropane and related compounds described in British patent specification Nos. 1,144,905 and 1,144,906. Another useful pharmaceutical composition comprises the Formula I compounds in combination with serotonin antagonists such as methysergide, the serotonin antagonists described in *Nature,* Vol. 316, pages 126–131, 1985, and the like. Each of the references referred to in this paragraph is hereby incorporated herein by reference.

The invention is further defined by reference to the following examples, which are intended to be illustrative and not limiting.

EXAMPLE 1

Ethyl 5,6-dichloro-3-methyl-4,7-benzofurandione-2-carboxylate

Ethyl 3-methyl-4,7-benzofurandione-2-carboxylate (0.5 g, 2 mmol) (from Example 25) was dissolved in acetic acid (75 mL) and $Cl_2$ gas wasbubbled in for 30 min. The reaction mixture was poured into $H_2O$ and the precipitate formed was filtered. Purification by re-crystallization gave the title product, mp 174°–175° C. 'HNMR (CDCl$_3$)δ: 1.4 (3H,t),2.55 (3H,s), 4.4(2H,q)

EXAMPLE 2

Ethyl 3,5,6-trimethyl-4,7-benzofurandione-2-carboxylate

Step 1. Ethyl 3-oxo-2-(3,4 dimethyl-2-methoxyphenoxy) butanoate

To a stirred solution of 3,4-dimethyl-2-methoxyphenol (101 g, 0.5 mole) in toluene (100 mL), cooled to 0° C., was added potassium hexamethyldisilazane (1.08 L, 0.675M in toluene). The solution was warmed to 80° C. over a period of 1h. The reaction was treated with ethyl 2-chloroacetoacetate (101 mL, 0.55 mole) and then heated to reflux for 3h. The reaction was cooled to RT and quenched with 25% NH$_4$OAc, and the products were extracted using EtOAc. Drying (Na$_2$SO$_4$) and evaporation of the solvent left a liquid which was fractionally distilled under vacuum (0.1 Torr) to give 3,4-dimethyl-2-methoxytrimethylsilyloxy benzene (bp 55°–100° C.) and 104 g of the title compound (bp 115°–6° C.)

Step 2. Ethyl 7-methoxy-3,5,6-trimethylbenzofuran-2-carboxylate

The material from Step 1 was cyclized to give the title compound using the method described by Royer* and Bisogn. Starting with 104 g of ketoester the title compound was obtained. 'HNMR (CDCl$_3$)δ = 1.40 (3H, t, J = 7.5 Hz), 2.27 (3H, s) 2.34 (3H,s), 2.52 (3H, s) 4.15 (3H, s) 4.42 (2H, q, J = 7.5 Hz), 7.07 (1H, s)

* Bull. Soc. Chim. Fr. 521, (1969)

Step 3. Ethyl 7-hydroxy-3,5,6-trimethylbenzofuran-2-carboxylate

To a solution of ethyl 7-methoxy-3,5,6-trimethylbenzofuran-2-carboxylate (97.2 g, 0.37 mole) (from Step 2) in dichloromethane (1 L) cooled to −78° C., was added a solution of BBr$_3$ (1.1 L, 1 M in dichloromethane). The reaction was warmed to −5° C. for and left for 15 mins. Quenching with 25% NH$_4$OAc buffer, extraction with EtOAc and drying (Na$_2$SO$_4$), followed by removal of solvent, afforded the product which was used as such for the following step.

'HNMR (CDCl$_3$)δ: 1.40 (3H, t, J=7.5 Hz) 2.27 (3H, s) 2.33 (3H, s), 2.50 (3H, s), 4.42 (2H, q, J = 1 7.5 Hz) 5.53 (1H broad s, OH), 6.95 (1H, s)

Step 4. Ethyl 3,5,6-timethyl-4,7-benzofurandione-2-carboxylate

The same procedure used to oxidize the phenol to the corresponding quinone in Example 3, Step 5 was employed to give the title compound from the compound of Step 3, mp 95°–96.5° C.

Analysis Calc'd: C, 64.12; H, 5.38; Found: C, 64.22; H, 5.41.

EXAMPLE 3

2-(4-methoxybenzyl) 3,5,6-trimethyl-4,7-benzofurandione

Step 1. 7-hydroxy-3,5,6-trimethylbenzofuran-2-carboxylic acid

Ethyl 7-hydroxy-3,5,6-trimethylbenzofuran-2-carboxylate (90 g, 0.37 mole) (from Example 2, Step 3) was dissolved in 1:1 MeOH/THF (600 mL) and cooled to 0° C. Dropwise addition of 2N NaOH (750 mL) followed by warming to room temperature for a 2 hr period effected saponification of the ester. The reaction was acidified with conc. HCl (150 mL) and the product extracted into EtOAc, dried (Na$_2$SO$_4$) and the solvent evaporated to give the carboxylic acid used directly in the next step.

Step 2. 7-Hydroxy-3,5,6-trimethylbenzofuran

The carboxylic acid from Step 1 (80 g, 0.37 mole) was dissolved in quinoline (750 mL) and Cu powder (16 g) was added to the solution. The reaction was heated to reflux for 90 min, cooled and 6N HCl (2L) was added. Extraction with EtOAc followed by chromatography on silica gel produced the title compound.

'HNMR (CDCl$_3$)δ: 2.22 (3H, d, J=1.5 Hz) 2.29 (3H, s) 2.37 (3H, s), 5.34 (1H, s, OH) 6.92 (1H, s), 7.32 (1H, q, J=1.5 Hz)

Step 3.
7-hydroxy-2-(4-methoxybenzoyl)-3,5,6-trimethylbenzofuran

To p-anisoyl chloride (205 g) in 1,2-dichloroethane (2 L), cooled to 0° C., was added AlCl$_3$ (240 g). The reaction mixture was warmed to room temperature and a solution of 7-hydroxy-3,5,6-trimethylbenzofuran (51 g) in 1,2-dichloroethane (400 mL) was added dropwise. The reaction was stirred for 5½ h then quenched with H$_2$O (2 L). The organic layer was separated and the aqueous layer was extracted with CH$_2$Cl$_2$. The combined extracts were washed with 25% NH$_4$OAc buffer, dried (Na$_2$SO$_4$) and filtered on silica gel to give 170 g of crude material which was used as such in the next step.

Step 4.
7-Hydroxy-2-(4-methoxybenzyl)-3,5,6-trimethylbenzofuran

The crude material from Step 3 was dissolved in ethylene glycol (600 mL) and KOH pellets (125 g) and anhydrous hydrazine (36 mL) were added. The reaction was heated to 150° C. for 2 hr, then cooled to RT (room temperature) and diluted with 10% NH$_4$OAc buffer (1.5 L) and the product was extracted into EtOAc. The crude product was chromatographed on silica gel (5% EtOAc/toluene) to yield the title compound, which was recrystallized in ether/hexane.

'HNMR (CDCl$_3$)δ: 2.17 (3H, s), 2.25 (3H, s), 2.34 (3H, s), 3.78 (3H, s), 4.01 (2H, s), 5.19 (1H, s, OH), 6.82 (2H, d, J=8 Hz), 6.84 (1H, s), 7.13 (2H, d, J=8 Hz)

Step 5.
2-(4-Methoxybenzyl)-3,5,6-trimethyl-4,7-benzofurandione

A solution of 7-hydroxy-2-(-4-methoxybenzyl)-3,5,6-trimethylbenzofuran from Step 4 (8.6 g, 29 mmol) in acetone (1.5 L) was added rapidly to a solution of potassium nitrosodisulfonate (Fremy's salt) (25 g, 93 mmol) in 0.055 M KH$_2$PO$_4$ buffer (1.5 L) at room temperature. The reaction was slowly heated to 45° C. over a period of 2 hr. The reaction was then cooled and the quinone was extracted with EtOAc (2x, 500 mL). Evaporation of the organic solvent gave a solid residue which was crystallized and re-crystallized from EtOH, to give the title compound, mp 111°-113° C.

Calc'd for C$_{18}$H$_{18}$O$_3$: C, 73.53; H, 5.84; Found: C, 73.54; H, 5.84

EXAMPLE 4
Ethyl 6-methoxy-3-methyl-5-propyl-4,7-benzofurandione-2-carboxylate Ethyl 4-hydroxy-6-methoxy-3-methylbenzofuran-2-carboxylate (7.1 mmol) was treated with K$_2$CO$_3$ (10.6 mmol) and allyl bromide (10.6 mmol) and heated in methyl ethyl ketone (50 mL) for 1h. The reaction was extracted into Et$_2$O and washed with 1% HCl, to give the allyl ether after drying and evaporation of the solvent.

The allyl ether was heated to reflux in O-dichlorobenzene for 40 min, and the rearranged 5-allyl product was purified by flash chromatography.

Hydrogenation with Pd-C catalyst (100 mg) in EtOH at 25-30 psi H$_2$ for 30 min followed by Fremy salt oxidation as in Example 3, Step 5 gave the title compound, mp 69°-70° C.

'HNMR (CDCl$_3$)δ: 0.95 (3H, t), 1.3-1.7 (5H, complex m) 1.50 (2H, dd), 1.60 (3H, s), 4.04 (3H, s), 4.38 (2H, q)

EXAMPLE 5
Ethyl 6-chloro-3-methyl-5-propyl-4,7-benzofurandione-2-carboxylate Following the procedure of Example 9, but starting with ethyl 3-methyl-5-propyl-4,7-benzofurandione-2-carboxylate, (from example 26) the title compound was obtained, mp 91.5°-93° C.

'HNMR (acetone-d6)δ: 0.98 (3H, t), 2.39 (3H, t), 1.50 (2H, Sextet), 2.60 (3H, s), 2.70 (2H, dd), 4.39 (3H, q).

EXAMPLE 6
Ethyl 3-methyl-5-propyl-6-ethylthio-4,7-benzofurandione-2-carboxylate Following the procedure Example 11 but starting with ethyl 3-methyl-5-propyl-4,7-benzofurandione-2-carboxylate (from Example 26) the title compound was prepared, m.p. 100°-101° C.

Analysis Calc'd: C, 60.70; H, 5.99; S. 9.53; Found: C, 60.43; H, 6.13; S, 10.09.

EXAMPLE 7
Ethyl 3-methyl-5-propyl-6-ethylsulfinyl-4,7-benzofurandione-2-carboxylate Following the procedure of Example 12 but starting with the product of Example 6. the title compound was prepared, mp 137°-138° C.

Analysis Calc'd: C, 57.94; H, 5.72; S. 9.10; Found: C, 58.27; H, 5.69; S, 10.29.

EXAMPLE 8
Ethyl 3-methyl-5-propyl-6-ethylsulfonyl-4,7-benzofurandione-2-carboxylate Following the procedure for Example 13, but starting with the product of Example 6, the title compound was prepared, mp 128°-129° C.

Analysis Calc'd: C, 65.98; H, 6.04; S. 8.01; Found: C, 65.89; H, 5.92; S, 8.51.

EXAMPLE 9
2-(3-Chloro-4-methoxybenzyl)-6-chloro-3-methyl-5-propyl-4,7-benzofurandione A solution of 2-(4-methoxybenzyl)-3-methyl-5-propyl-4,7-benzofurandione (from Example 28) (0.5 g) in AcOH (10 mL) was saturated with gaseous Cl$_2$ for 5 minutes. Chromotagrphy on silica gel afforded the title compound, mp 134.5°-136° C.

'HNMR (CDCl$_3$)δ: 1.01 (3H, t), 1.4-1.6 (2H, sextet), 2.29 (3H, s), 2.68 (2H, dd), 3.90 (3H, s), 4.00 (2H, s), 6.86 (1H, d), 7.11 (1H, dd), 7.20 (1H, d).

EXAMPLE 10
3,6-Dimethyl-2-(4-methoxybenzyl)-5-propyl-4,7-benzofurandione A solution of 2-(4-methoxybenzyl)-3-methyl-5-propyl-4,7-benzofurandione (from Example 28) (0.36 g, 1.1 mmol) is EtOAc (50 mL) was stirred over an aqueous solution of Na$_2$S$_2$O$_4$ (sat'd) for 16 hours. The EtOAc layer was separated, dried (MgSO$_4$) and the solvent removed to give a solid residue. This residue was dissolved in 1,2-dichloroethane (10 mL) and N,N-dimethylmethyleneammonium iodide (725 mg) was added.

The reaction was heated to 60° C. for 3h, then EtOH (10 mL) was added followed by NaBH$_4$ (0.4 g). The reaction was heated to reflux for 20 min. Saturated NH$_4$Cl was added and the product was extracted with Et$_2$O to give the title compound, mp 114°–114.5° C.

Analysis Calc'd: C, 74.54; H, 6.55; Found: C, 74.22; H, 6.30.

EXAMPLE 11

2-(4-methoxybenzyl)-3-methyl-5-propyl-6-ethylthio-4,7-benzofurandione

To a suspension of 2-(4-methoxybenzyl)-3-methyl-5-propyl-4,7-benzofurandione (from Example 28) (0.988 g, 3.05 mmol) in MeOH (23 mL) was added ethanethiol (2.5 mL). After a few minutes, the yellow quinone passed into solution giving a reddish colour. The reaction was cooled to 0° C. and solid FeCl$_3$ (2.5 g) was added. The reaction was quenched 10% HCl and extraction with CH$_2$Cl$_2$ afforded the crude product which was chromatographed on silica gel (5% EtOAc/hexane) to yield the title compound.

Analysis Calc'd: C, 68.72; H, 6.29; S. 8.34; Found: C, 68.44; H, 6.09; S, 9.02.

EXAMPLE 12

2-(4-methoxybenzyl)-3-methyl-5-propyl-6-ethylsulfinyl-4,7-benzofurandione

To a solution of the product of Example 11 (247 mg, 0.66 mmol) in CH$_2$Cl$_2$ (30 mL) was added m-chloroperbenzoic acid (140 mg). The reaction was complete in a few minutes, and was quenched with 10% NaCO$_3$. The organic layer was separated, dried (Na$_2$SO$_4$) and the crude product was chromatographed on silica gel (30% EtOAc/hexane) to give the title compound.

Analysis Calc'd: C, 65.98; H, 6.04; S. 8.01; Found: C, 65.89; H, 5.92; S, 8.51.

EXAMPLE 13

2-(4-methoxybenzyl)-3-methyl-5-propyl-6-ethylsulfonyl-4,7-benzofurandione

To a solution of the product of Example 11 (259 mg, 0.67 mmol) in CH$_2$Cl$_2$ (25 mL) was added m-chloroperbenzoic acid (289 mg). After 5h the reaction was completed. The reaction was worked up following the procedure of Example 12 to yield the title compound.

Analysis Calc'd: C, 63.44; H, 5.81; S. 7.70; Found: C, 63.19; H, 5.96; S, 8.35.

EXAMPLE 14

6-Amino-2-(4-methoxybenzyl)-3-methyl-5-propyl-4,7-benzofurandione

To a solution of 2-(4-methoxybenzyl)-3-methyl-5-propyl-4,7-benzofurandione (from Example 28) (295 mg, 0.91 mmol) in MeOH (3 mL) were added NH$_4$Cl (109 mg) and NaN$_3$ (130 mg). The mixture was heated to reflux for 4 hours and the solvent was then removed in vacuo. Water was added and the product was extracted into CH$_2$Cl$_2$ and chromatographed on silica gel (15% EtOAc/hexane) to give the title compound.

'HNMR (CDCl$_3$)δ: 0.96 (3H, t, J - 7.1 Hz), 1.46 (2H, m), 2.24 (3H, s), 2.30 (2H, dd, J - 6.7 and 7.8 Hz), 3.78 (3H, s), 3.97 (2H, s), 4.88 (2H, broad s), 6.83 (2H, d, J - 9.0 Hz), 7.13 (2H, d, J=9.0 Hz).

EXAMPLE 15

3,5-Dimethyl-2-(4-methoxybenzyl)-6-propyl-4,7-benzofurandione

Starting with 7-hydroxy-3-methyl benzofuran, the corresponding 7-hydroxy-3-methyl-6-propyl benzofuran was prepared using the procedure described in Example 4. The 2-(4-methoxybenzyl) compound was formed according to the procedure of Example 3 (Steps 3 and 4). Finally Fremy's salt oxidation according to Example 3, Step 5 gave 2-(4-methoxybenzyl)-3-methyl-6-propyl-4.7-benzofurandione.

Following the procedure of Example 10, but starting 2-(4-methoxybenzyl)-3-methyl-6-propyl-4,7-benzofurandione, the title compound was obtained, m.p. 60°–61° C.

Analysis Calc'd: C, 74.54; H, 6.55; Found: C, 74.57; H, 6.61.

EXAMPLE 16

2-(4-hydroxybenzyl)-3,5,6-trimethyl-4,7-benzofurandione

Following the procedure of Example 2, Step 3, but starting with the product of Example 3, the title compound was obtained.

'HNMR (CDCl$_3$)δ: 2.00 (3H, s), 2.04 (3H, s), 2.23 (3H, s), 3.92 (2H, s), 5.7 (1H, bs, OH), 6.77 (2H, d), 7.02 (2H, d).

EXAMPLE 17

2-Ethyl-3,5,6-trimethyl-4,7-benzofurandione

Following the procedure of Example 3, Steps 3–5, but using acetyl chloride in place of p-anisoyl chloride in Step 3, the title compound was obtained.

'HNMR (CDCL$_3$)δ: 1.25 (3H, t), 2.05 (3H, s), 2.11 (3H, s), 2.21 (3H, s), 2.72 (2H, q)

EXAMPLE 18

2-(3,4-methylenedioxybenzyl)-3,5,6-trimethyl-4,7-benzofurandione

Following the procedure of Example 3, Steps 3–5, but using 3,4-methylenedioxybenzoyl chloride in place of p-anisoyl chloride in Step 3, the title compound is obtained.

EXAMPLE 19

2-[2-(4-methoxyphenyl) ethyl]-3,5,6-trimethyl-4,7-benzofurandione

Following the procedure of Example 3, Steps 3–5, but using 4-methoxyphenylacetyl chloride in place of p-anisoyl chloride in Step 3, the title compound is obtained.

EXAMPLE 20

2-[1-(4-methoxyphenyl) ethyl]-3,5,6-trimethyl-4,7-benzofurandione

To 7-hydroxy-2-(4-methoxybenzoyl)-3,5,6-trimethyl benzofuran (250 mg) (from Example 3, Step 3) in THF (6 mL) was added MeLi (1.6M/Et$_2$O, 0.84 ml). The reaction was quenched with 25% NH$_4$OAc and the product was extracted with Et$_2$O. The tertiary alcohol was treated with LiAlH$_4$ (0.4 g) and AlCl$_3$ (0.35 g) in Et$_2$O (20 mL). The reaction was complete in 15 min and Fremy's salt oxidation of the crude material according to Example 3, Step 5 provided the title compound.

'HNMR (CDCl$_3$)δ: 1.68 (3H, d), 2.04 (3H, s), 2.08 (3H, s), 2.17 (3H, s), 3.75 (3H, s), 4.23 (2H, q), 6.83 (2H, d), 7.17 (2H, d).

EXAMPLE 21

2-phenylthio-3,5,6-trimethyl-4,7-benzofurandione

Step 1 4,7-Dimethoxy-3,5,6-trimethylbenzofuran

A solution of 3,5,6-trimethyl-4,7-benzofurandione obtained by Fremy salt oxidation of 7-hydroxy-3,5,6-trimethylbenzofuran (Example 3, Step 2) (2.5 g, 13 mmol) in EtOAc (100 mL) was stirred together with a saturated solution of Na$_2$S$_2$O$_4$ (100 mL) for 16h. The organic layer was separated, collected and dried (Na$_2$SO$_4$), and evaporated to dryness leaving a solid white residue. The crude residue was added to a suspension of NaH (0.72 g, 30 mmol) in dry DMF (50 mL) and maintained at 0° C. Methyl iodide (9.2 g, 65 mmol) was added and the reaction was warmed to RT over a 2h period. Addition of Et$_2$O followed by thorough washing with H$_2$O (5x) afforded an etherial solution of the title compound. The organic phase was dried (MgSO$_4$) and the ether was evaporated to give a residue which was chromatographed on silica gel (20% CH$_2$Cl$_2$/EtOAc) to give the title compound.

'HNMR (CDCl$_3$)δ: 2.48 (s, 3H, CH$_3$), 2.51 (s, 3H, CH$_3$), 2.59 (d, 3H, CH$_3$) 3.02 (s, 3H, )CH$_3$), 3.27 (s, 3H, OCH$_3$, 6.50 (q, 1H, aromatic H).

Step 2.
4,7-Dimethoxy-2-phenylthio-3,5,6-trimethylbenzofuran

To a solution of 4,7-dimethoxy-3,5,6-trimethylbenzofuran from Step 1 (155 mg, 0.7 mmol) in n-Bu$_2$O (1 mL) was added nBuLi (0.5 mL, 0.8 mmol, 1.6 M hexanes) at RT and the reaction was stirred for 2h. Diphenyl disulfide 220 mg, 1 mmol) was added and the reaction was stirred overnight. Addition of Et$_2$O and washing (2x) H$_2$O followed by drying (Na$_2$SO$_4$) and concentration gave a Bu$_2$O solution of the crude product, which was chromatographed on silica gel (5% EtOAc/hexane) to afford the title compound.

'HNMR (CDCl$_3$)δ: 2.26 (3H, s, CH$_3$), 2.27 (3H, s, CH$_3$), 2.49 (3H, s, CH$_3$), 3.82 (3H, s, OCH$_3$), 4.04 (3H, s, OCH$_3$), 7.1–7.3 (5H, m, aromatic).

Step 3.
2-Phenylthio-3,5,6-trimethyl-4,7-benzofurandione

A solution of 4,7-dimethoxy-2-phenylthio-3,5,6-trimethylbenzofuran from Step 2 (200 mg, 0.64 mmol) in CH$_2$Cl$_2$ (10 mL) was cooled to −78° C. and a BBr$_3$ solution (2.8 mL, 2.8 mmol, 1M CH$_2$Cl$_2$) was added dropwise. The reaction was slowly warmed to room temperature then quenched with 25% NH$_4$OAc. Extraction with EtOAc followed by addition of Powdered FeCl$_3$ and flash chromatography on silica gel (10% EtOAc/hex) afforded the title compound.

Calc'd for C$_{17}$H$_{14}$O$_3$S: C, 68.43; H, 4.73; S, 10.75; Found C, 68.65; H, 4.66; S, 11.23.

EXAMPLE 22

Methyl (3,5,6-trimethyl-4,7-benzofurandion-2-yl)thioacetate

Following the procedure of Example 21, Steps 2 and 3, but using dimethyl dithiodiacetate in place of diphenyldisulfide the title compound was obtained.

'HNMR (acetond-d$_6$)δ: 2.05 (3H, s), 2.06 (3H, s), 2.30 (3H, s), 3.57 (2H, s), 3.71 (3H, s).

EXAMPLE 23

(3,5,6-Trimethyl-4,7-benzofurandion-2-yl)thioacetic acid

Following the procedure of Example 3, Step 1, but starting with the product of Example 22, the title compound was obtained.

'HNMR (acetone d$_6$)δ: 2.22 (3H, s), 2.24 (3H, s), 2.45 (3H, s), 3.58 (2H, s).

EXAMPLE 24

2-phenyl-3,5,6-trimethyl-4,7-benzofurandione

Step 1.
2-phenyl-4,7-dimethoxy-3,5,6-trimethylbenzofuran

A solution of 4,7-dimethoxy-3,5,6-trimethylbenzofuran (from Example 21, Step 1) (1.98 g, 9.0 mmol) in n-Bu$_2$O (12 mL) was treated with n-BuLi (6.0 mL, 1.6 M/hexanes) at 25° C. to form the 2-lithio species. THF (10 mL) was added followed by CuBr-Me$_2$S (1.9 g), phenyl iodide (1.2 mL) and pyridine (20 mL). The reaction was heated to reflux for 6h. Hydrolysis with 10% HCl and extraction with EtOAc, followed by chromatography on silica gel (20% C$_6$H$_6$/CCl$_4$) afforded the title compound.

'HNMR (C$_6$D$_6$)δ: 2.24 (3H, s), 2.26 (3H, s), 2.47 (3H, s), 3.79 (3H, s), 4.08 (3H, s), 7.33 (1H, t), 7.44 (2H, t), 7.77 (2H, d).

Step 2. 2-phenyl-3,5,6-trimethyl-4,7-benzofurandione

Following the procedure for Example 21, Step 3, but using the product of Example 24, Step 1, the title compound was prepared.

'HNMR (CDCl$_3$)δ: 2.03 (3H, s), 2.06 (3H, s) 2.49 (3H, s), 7.3–7.5 (3H, m, aromatic), 7.68 (2H, dd, aromatic).

The starting materials for some of the Examples are to be found in the following publications:
Example 25: W. B. Whalley, J. Chem. Soc. 3229–3235 (1951)
Example 26; European patent application No. 146,243 (June 26, 1985) and
Example 28: European patent application No. 165,810 (Dec. 27, 1985)

EXAMPLE 25

Ethyl 3-methyl-4,7-benzofurandione-2-carboxylate

A mixture of ethyl 4-hydroxy-3-methylbenzofuran-2-carboxylate (2.2 g; 10 mmoles), N,N'-Bis (salicylidene) ethylenediaminocobalt (II) hydrate (650 mg; 2 mmoles) and N,N-dimethylformamide (50 ml) was stirred for 18 hours as oxygen was gently bubbled through the mixture. The mixture was diluted with diethyl ether (200 ml) and filtered. The filtrate was washed with H$_2$O (50 ml) three times, dried over sodium sulfate, filtered and evaporated. Trituration with a small volume of diethyl ether and filtration yielded the title compound, physical data for which are shown in Table 4. Following the above described procedures, the compounds of Table 3 were prepared. In Table 4 are shown the physical data for Examples 25–31

TABLE 3

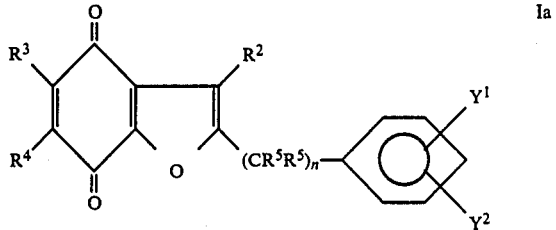

| Ex. No. | $R^1$ | $Y^1$ | $Y^2$ | $R^3$ |
|---|---|---|---|---|
| 25 | $CO_2Et$ | — | — | H |
| 26 | $CO_2Et$ | — | — | n-Pr |
| 27 | H | — | — | n-Pr |
| 28 | $CH_2C_6H_3Y^1Y^2$ | 4-OMe | H | n-Pr |
| 29 | $CH_2C_6H_3Y^1Y^2$ | 4-OH | H | n-Pr |
| 30 | $CH_2C_6H_3Y^1Y^2$ | 4-OMe | H | H |
| 31 | $CH_2CO_2Et$ | — | — | n-Pr |

TABLE 4

| Ex. No. | m.p. (°C.) | ANALYSIS OR $^1H$—NMR |
|---|---|---|
| 25 | 105–107 | Analysis Calc'd: C, 61.53; H, 4.30<br>Found: C, 61.90; H, 4.03 |
| 26 | 63–66 | Analysis Calc'd: C, 65.20; H, 5.83<br>Found: C, 65.12; H, 5.82 |
| 27 | 72–74 | Analysis Calc'd: C, 70.57; H, 5.92<br>Found: C, 70.50; H, 5.57 |
| 28 | 84–86 | Analysis Calc'd: C, 74.05; H, 6.20<br>Found: C, 74.06; H, 6.34 |
| 29 | | $^1H$—NMR (CDCl$_3$) δ: 0.9 (3H, t), 1.4 (2H, m), 2.3 (3H, s), 2.4 (2H, t), 3.95 (2H, s), 6.5 (1H, s), 6.8 (2H, d), 7.1 (2H, d) |
| 30 | 129–131 | |
| 31 | | Analysis Calc'd: C, 66.19; H, 6.29<br>Found: C, 65.58; H, 6.36 |

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

What is claimed is:

1. A compound of the formula:

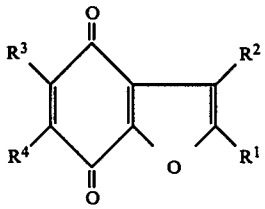

$R^1$ is

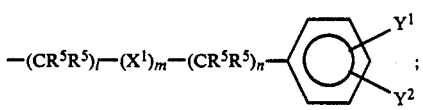

—$(CR^5R^5)_s$—$(X^1)_t$—$(CR^5R^5)_u$—$CO_2R^6$; or lower alkyl;

$R^2$ is lower alkyl;
$R^3$ and $R^4$ are each independently $R^2$, Cl, $X^2R^2$, or $X^3R^5$;
$R^5$ is H or lower alkyl, or two $R^5$'s when attached to N may be joined to form a 5- or 6-membered ring;
$R^6$ is H or lower alkyl;
$R^7$ is H or lower alkyl;
$R^8$ is H or lower alkyl;
$X^1$ is $X^2$ or $X^3$;
$X^2$ is S, S(O), S(O)$_2$;
$X^3$ is O or $NR^5$;
$X^4$ is $X^2$ or $X^3$
$Y^1$ and $Y^2$ are each independently: H, $R^2$, $X^2R^2$, $X^3R^5$, halogen, $(X^4)_w$—$(CR^5R^5)_z$—$CO_2R^7$, $CF_3$, $COR^8$, $CONR^5R^5$, or $S(O_2)NR^5R^5$; or $Y^1$ and $Y^2$ may be joined to form a 5- or 6-membered ring, containing one or two O atoms;
l and n are each independently 0 to 5;
m is 0 or 1;
s is 0 to 3;
u is 0 to 3 provided that when t is 1 and $R^6$ is H, then u is 1 to 3;
t is 0 or 1;
w is 0 or 1; and
z is 0 to 3, Provided that when w is 1 and $R^7$ is H, then z is 1 to 3; wherein lower alkyl is a straight, branched or cyclic alkyl of 1–7 carbons; and the pharmaceutically acceptable salts thereof.

2. A compound of claim 1 which is represented by Formula Ia:

Ia wherein:
$R^3$ is $R^2$
$R^4$ is $R^2$ or $X^3R^5$
n is 0 or 1
and the remaining substituents are as defined for Formula I.

3. A compound of claim 1 wherein:
$R^1$ is lower alkyl; $R^3$ and $R^4$ are each independently $R^2$, $X^2R^2$, or $X^3R^5$; and the remaining substituents are as defined for Formula I.

4. A compound of claim 1 which is:
Ethyl 5,6-dichloro-3-methyl-4,7-benzofurandione-2-carboxylate;
Ethyl 3,5,6-trimethyl-4,7-benzofurandione-2-carboxylate;
2-(4-Methoxybenzyl)-3,5,6-trimethyl-4,7-benzofurandione;
Ethyl 6-methoxy-3-methyl-5-propyl-4,7-benzofurandione-2-carboxylate;
Ethyl 6-chloro-3-methyl-5-propyl-4,7-benzofurandione-2-carboxylate;
Ethyl 3-methyl-5-propyl-6-ethylthio-4,7-benzofurandione-2-carboxylate;
Ethyl 3-methyl-5-propyl-6-ethylsulfinyl-4,7-benzofurandione-2-carboxylate;
Ethyl 3-methyl-5-propyl-6-ethylsulfonyl-4,7-benzofurandione-2-carboxylate;

2-(3-Chloro-4-methoxybenzyl)-6-chloro-3-methyl-5-propyl-4,7-benzofurandione;

3,6-Dimethyl-2-(4-methoxybenzyl)-5-propyl-4,7-benzofurandione;

2-(4-Methoxybenzyl)-3-methyl-5-propyl-6-ethylthio-4,7-benzofurandione;

2-(4-Methoxybenzyl)-3-methyl-5-propyl-6-ethylsulfinyl-4,7-benzofurandione;

2-(4-Methoxybenzyl)-3-methyl-5-propyl-6-ethylsulfonyl-4,7-benzofurandione;

6-Amino-2-(4-methoxybenzyl)-3-methyl-5-propyl-4,7-benzofurandione;

3,5-Dimethyl-2-(4-methoxybenzyl)-6-propyl-4,7-benzofurandione;

2-(4-hydroxybenzyl)-3,5,6-trimethyl-4,7-benzofurandione;

2-Ethyl-3,5,6-trimethyl-4,7-benzofurandione;

2-(3,4-Methylenedioxybenzyl)-3,5,6-trimethyl-4,7-benzofurandione;

2-[2-(4-Methoxyphenyl) ethyl]-3,5,6-trimethyl-4,7-benzofurandione;

2-[1-(4-Methoxyphenyl) ethyl]-3,5,6-trimethyl-4,7-benzofurandione;

2-Phenylthio-3,5,6-trimethyl-4,7-benzofurandione;

Methyl (3,5,6-trimethyl-4,7-benzofurandion-2-yl)thioacetate;

(3,5,6-Trimethyl-4,7-benzofurandion-2-yl)thioacetic acid; or

2-Phenyl-3,5,6-trimethyl-4,7-benzofurandione.

5. A compound of claim 1 which is:

| $R^1$ | $Y^1$ | $Y^2$ | $R^2$ | $R^3$ | $R^4$ |
|---|---|---|---|---|---|
| $CH_2C_6H_3Y^1Y^2$ | 4-OMe | H | Me | Me | Me |
| $CH_2C_6H_3Y^1Y^2$ | 4-OMe | H | Me | n-Pr | $NH_2$ |
| $CH_2C_6H_3Y^1Y^2$ | 4-OH | H | Me | Me | Me |
| Et | — | — | Me | Me | Me |
| $CH(CH_3)C_6H_3Y^1Y^2$ | 4-OMe | H | Me | Me | Me |
| $C_6H_3Y^1Y^2$ | H | H | Me | Me | Me |

6. A pharmaceutical composition useful in inhibiting leukotriene biosynthesis in mammals in need thereof comprising an amount of a compound of claim 1 effective as a leuktriene biosynthesis inhibitor and a pharmaceutically acceptable carrier.

7. The pharmaceutical composition of claim 6 additionally comprising an effective amount of a second active ingredient selected from the group consisting of non-steroidal anti-inflammatory drugs; peripheral analgesic agents; cyclooxygenase inhibitors; leukotriene antagonists; leukotriene inhibitors; $H_2$-receptor antagonists; antihistaminic agents; prostaglandin antagonists; and thromboxane antagonists.

8. A pharmaceutical composition according to claim 7, wherein the second active ingredient is a non-steroidal anti-inflammatory drug.

9. The pharmaceutical composition of claim 7, wherein the weight ratio of compound of Formula I to said second active ingredient ranges from about 1000:1 to about 1:1000.

10. A method of inhibiting leukotriene biosynthesis in mammals in need therof which comprises administering to a mammal an inhibitory effective amount of a compound of claim 1.

11. A method of treating or ameliorating allergic conditions, asthma, psoriasis, pain, inflammation, or cardiovascular conditions in mammals or inducing cytoprotection in mammals comprising administering to a mammal in need of said treatment an effective amount of a compound of claim 1.

12. A compound of claim 1 wherein $Y^1$ and $Y^2$ form —$OCH_2O$—, —$OCH_2CH_2O$—, —$OCH_2CH_2$— or —$OCH_2CH_2CH_2$—.

* * * * *